United States Patent [19]

Polchaninoff

[11] 4,426,884

[45] Jan. 24, 1984

[54] FLEXIBLE FORCE SENSOR

[75] Inventor: Michael Polchaninoff, Huntington, N.Y.

[73] Assignee: The Langer Biomechanics Group, Inc., Deer Park, N.Y.

[21] Appl. No.: 351,961

[22] Filed: Feb. 24, 1982

[30] Foreign Application Priority Data

Feb. 1, 1982 [GB] United Kingdom ................ 8202830

[51] Int. Cl.³ .......................... A61B 5/00; H01C 10/10
[52] U.S. Cl. ........................................ 73/172; 338/47; 338/114
[58] Field of Search ................ 73/172, 862.64, 862.68; 338/47, 99, 114

[56] References Cited

U.S. PATENT DOCUMENTS

| | | | |
|---|---|---|---|
| 2,752,558 | 6/1956 | Kane | 73/725 |
| 3,509,296 | 4/1970 | Harshman et al. | 338/114 |
| 4,257,305 | 3/1981 | Friend et al. | 338/114 |

*Primary Examiner*—S. Clement Swisher
*Attorney, Agent, or Firm*—James & Franklin

[57] ABSTRACT

The flexible force sensor having an electrical conductor releasably attachable to a test site and a plurality of relatively spaced electrical contacts supported for varying contact with the conductor such that when a force is applied to the force sensor, the electrical contacts and electrical conductor move into and out of varying areas of electrical contact to produce electrical resistances therebetween corresponding to the extent of such contact and as a function of the applied force.

24 Claims, 13 Drawing Figures

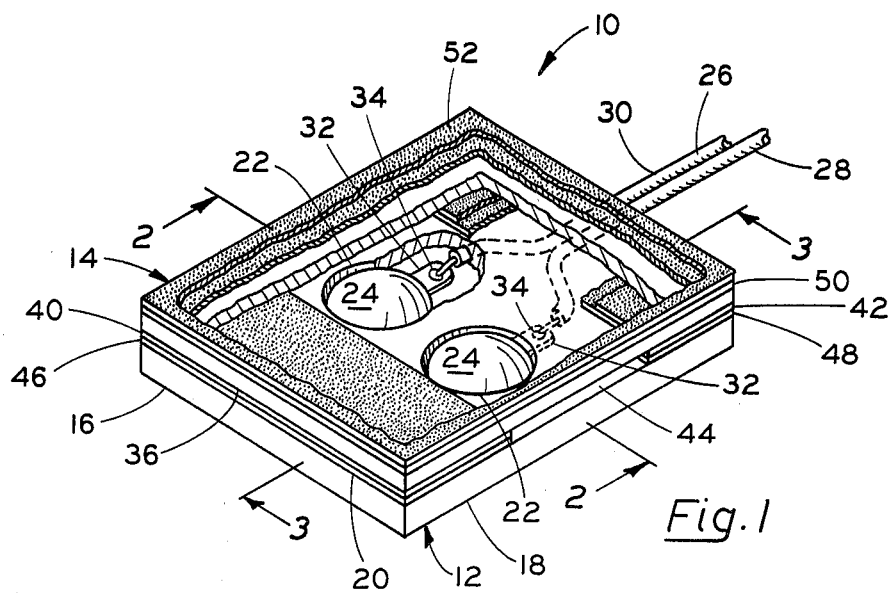
Fig.1
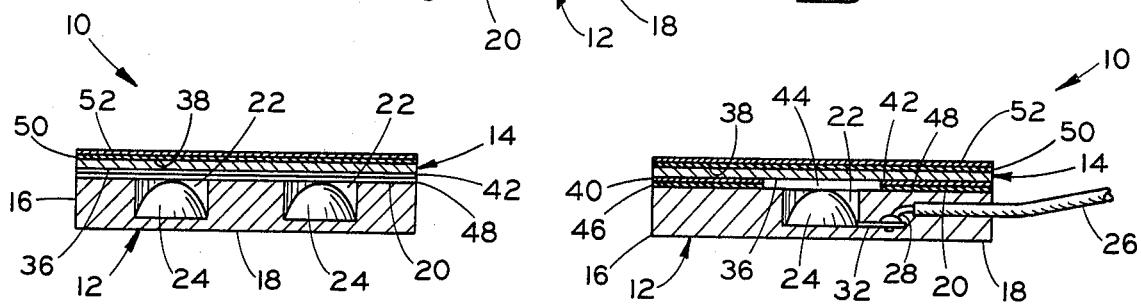
Fig.2     Fig.3
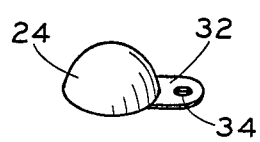
Fig.4
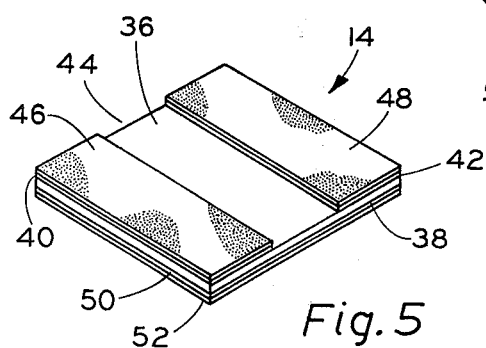
Fig.5
Fig.6
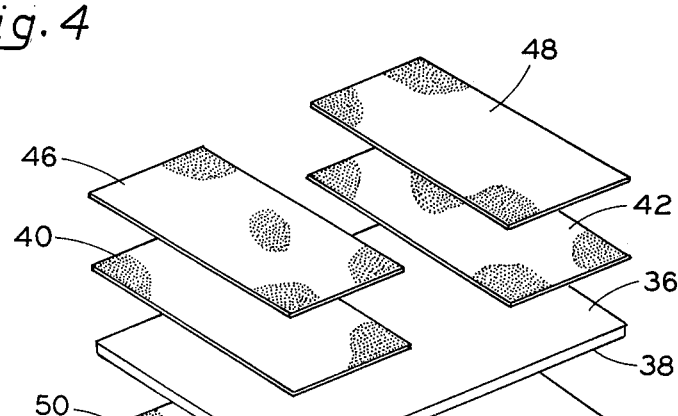
Fig.7

FLEXIBLE FORCE SENSOR

This invention relates to a sensor. More particularly, the invention relates to an inexpensive disposable sensor that can be used to sense forces exerted by the human body during such movements as walking, jogging and in orthopedic testing.

In recent years studies of human gait by orthopedic testing involve the accumulation of quantitative measurements of the forces exerted by the foot against the ground. Such information has proven particularly effective in diagnosing and treating neurological and muscular abnormalities. Such studies are described in, for example, U.S. Pat. No. 2,290,387. Studies of the human gait have also been found useful in the diagnosis and treatment of orthopedic foot disorders. An example of such a study is described in L. F. Dragnich et al. *Measurement of Instantaneous Foot-Floor Contact Patterns,* Orthopedic Research Society, Orthopedic Transactions 1980, Vol. 4 #2 at p. 242.

Recently, human gait studies have been used for both diagnosis and treatment in sports medicine and biomechanics. These studies are used analytically to measure the force and movement generated by an athlete's foot during training and competition. Based on such measurements, special training exercises and techniques have been devised to improve the athlete's competitive performance.

A number of different types of measuring devices are employed to measure the forces exerted by a subject during movements, as in walking, running or the like. For example, U.S. Pat. No. 2,095,268 describes an orthopedic pressure sensing device which employs a fluid-containing diaphragm. As a subject stands and walks on the device, the pressure applied to the diaphragm is measured. Similar fluid-containing diaphragms are also described in two U.S. Pat. Nos. 2,192,435 and 3,974,491.

Electrical means for measuring human gait is taught in the above-mentioned U.S. Pat. No. 2,290,387. Piezoelectric multicomponent measuring platforms have been marketed for a number of years. For example, a quartz multi-component measuring platform is marketed by Kistler Instruments A. G. of Wintertherm, Switzerland. More recently, multiaxial load cells employing small foil type strain gauges have been incorporated in a subject's shoe to measure gait. See, for example, H. S. Ranu et al, *A Study of Normal and Abnormal Human Gait With Miniature Triaxial Shoe-Borne Load Cells,* Orthopedic Research Society, Orthopedic Transactions 1980, Vol. 4 #2 at p. 240.

These prior art devices for measuring gait all have numerous disadvantages. For example, fluid filled diaphragm devices have proven inaccurate. Further, it has been found that devices which utilize either a platform or pad on which a subject stands, or a specially fitted shoe which must be worn by a subject, are cumbersome and difficult to use. Rigid or bulky sensors mounted in shoes or on the body are uncomfortable and this discomfort has been known to affect the validity of the test since it may affect a subject's movements or gait. Moreover, when the sensor is placed in a shoe, the shoe is specially modified to accommodate the sensor such that the shoe must be discarded after such special use.

The present invention ovecomes several of the above-noted drawbacks of prior devices. In general, and in the present invention, force measurement is accomplished by an induced change in the electrical resistance of the sensor system. This change in electrical resistance is in response to and in correspondence with the applied force. The inventive force sensor is an inexpensive two-part device and, as such, comprises a reusable permanent electrode platform and a flexible, relatively thin, inexpensive, elastomeric conductive sensor pad that may be disposable. The latter is intended to be releasably attached to a selected test site of a subject's skin.

The permanent electrode includes curved or dome-like metallic contacts generally of hemispherical configuration supported thereon or embedded therein and adapted to touch or be closely positioned to electrical circuit engagement with the sensor pad when the pad and permanent electrode are detachably joined. When the permanent electrode is attached to or joined with the sensor pad, the curved or dome-like contacts are placed in facing opposition to the conductive sensor pad. When a compressive load is applied across the sensor, the sensor pad and metallic contacts are, to varying extents, pressed together thus inducing a change in the surface area of contact therebetween.

The surface area of contact between the latter and former is proportional to or modulated by the applied force. When the magnitude of the applied force is relatively small, the surface area of engagement between each metal contact and an associated facing region of sensor pad is small. When the magnitude of the applied force increases, the sensor pad and contacts are driven more firmly together causing the sensor pad to envelop and engage the metallic contacts to a greater degree, thus increasing the surface area of contact between them. Small area of contact between the dome-like metallic contacts and conductive sensor pad equals a relatively high resistance, and conversely, large area of contact between the dome-like members and respective portions of the conductive sensor pad equals a relatively low resistance.

This change in resistance is easily monitored by appropriate instrumentation. When the test is completed, the electrode assembly is readily removed from the skin or test site. The disposable sensor pad is readily detached from the permanent electrode and discarded. A force sensor built according to the present invention can be constructed so as to be unusually thin and thus present a minimal feeling of presence or discomfort in use.

It is therefore an object of the present invention to provide a durable force sensor of thin, planar, flexible construction.

It is another object of the present invention to provide a thin, flexible sensor for use in measuring the forces exerted by the human body which is comprised of two parts, one part being a permanent electrode and the other part being a conductive sensor pad adapted to be attached to the skin at a given test site and which is inexpensive so it can be discarded after use.

It is a further object of the present invention to provide a thin, flexible force sensor for use on the human body wherein the sensor is comprised of two parts detachably joined together so that that part of the sensor which is in immediate contact with the body can be discarded after use thereby to facilitate sanitary test procedures.

It is another object of the present invention to provide a pressure transducer adapted to measure forces exerted by the human body wherein the transducer is of minimal thickness, employs a change in electric resistance as a parameter corresponding to the applied force, and which is low in cost.

Other objects and features of the present invention will become apparent from the following detailed description considered in connection with the accompanying drawings. It is understood, however, that the drawings are designed for purposes of illustration only, and not as a definition of the limits of the invention for which reference should be made to the appending claims.

In the drawings, wherein the same reference numeral denotes the same element throughout the several view:

FIG. 1 is an enlarged perspective view of the inventive sensor or transducer assembled but with parts thereof broken away;

FIG. 2 is a cross-sectional view taken along the line 2—2 of FIG. 1 showing the electrical contacts of the permanent electrode;

FIG. 3 is a cross-sectional view taken along the line 3—3 of FIG. 1;

FIG. 4 is a perspective view of an electrical contact employed as part of the permanent electrode;

FIG. 5 is a perspective view of the inner or electrode-facing side of the assembled disposable sensor pad;

FIG. 6 is a perspective view of the outer side of the sensor pad of FIG. 5;

FIG. 7 is an exploded perspective view of the sensor pad seen in FIG. 5;

Figure 8:
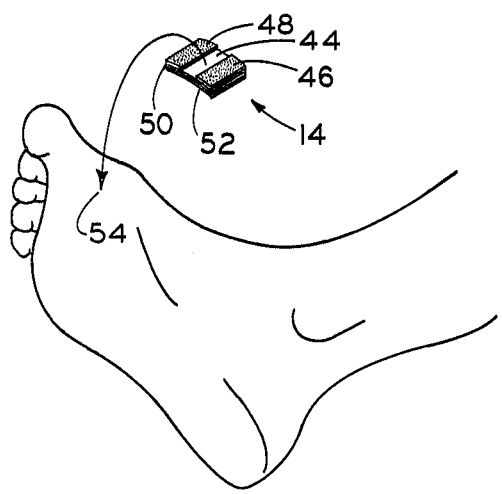
FIGS. 8, 9 and 10 are each diagrammatic perspective views showing the selection of a test site on the body and how the inventive sensor is attached to the test site.
Figure 9:
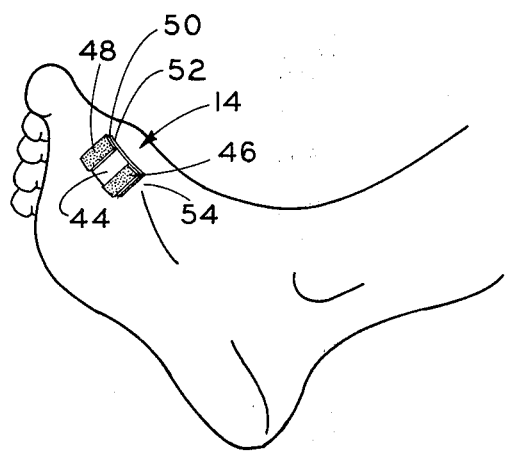

Referring to FIGS. 1 through 12, the force sensor of the present invention is indicated generally by the reference numeral 10. Sensor 10 is comprised of two complementary sized mating members or parts. One is a permanent reusable electrode generally identified by numeral 12 and the other is a disposable conductive sensor pad generally identified 14 that is detachably, yet adhesively, bonded or otherwise joined to the test site of a selected part of the body. Permanent electrode 12 is preferably formed as a relatively thin member 16 of inexpensive non-conductive elastomeric material and is defined by two spaced substantially planar faces 18 and 20.

The member 16 of the permanent electrode 12 is substantially planar, made relatively thin, sheet-like and flexible so as to conform to the bending movements of the skin or test site of a human to which the same is attached thereby avoiding interference with the comfort of the wearer. In practice, it has been made of a soft, compressible, flexible urethane elastomer of the type manufactured by E. P. DuPont De Nemours Company of Wilmington, Del. The urethane elastomer is well suited for its intended purpose because it has the characteristics of silicone rubber and is a dielectric material that functions as an electrical insulator. The structure 12 is here referred to as the permanent electrode for convenience only because it is intended to be reused, whereas the conductive pad 14 is intended to be disposed of or thrown away after only one use for sanitary reasons.

The member 16 may be molded with one or more positioning means 22 defined or formed therein that may take the form of wells or sockets that open at and communicate with the inner face 20. These positoning means 22 are apertures that function to mount or support one or more of a plurality of electrically conductive contact elements 24 in insulating spaced relationship. As the description proceeds, it will be clear that the contacts 24 may be molded integral with the member 16 so as to be formed as a unitary part thereof. In the present embodiment there are two such positioning means 22 with each properly containing a respective contact element 24 therein.

Figure 11:
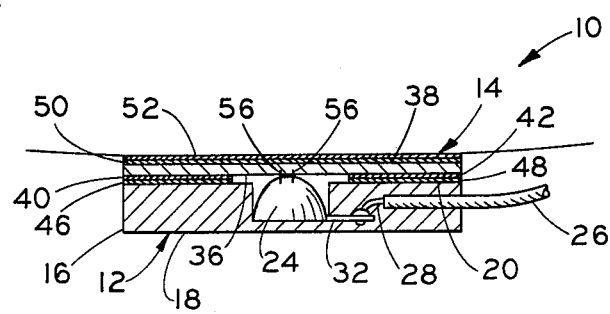
FIG. 11 is a cross-sectional view of the sensor as shown in FIG. 3 attached to a test site as in FIG. 10 to illustrate its details when no pressure is applied.

The contact elements 24 each are formed of a conductive material that has a curved outer surface facing outward from its positioned, supported end and extends toward the opening of its respective aperture or well 22. For ease of description, the extent and form of curvature or shape of the contact elements 24 may be described as domed or hemispherical, with the smallest area of the curve thereof being at or substantially in or beyond the plane of that of the inner face 20. When the contacts extend outward and beyond the plane of the inner face 20, it is possible that the curved dome of the contact 24 may or may not be in initial touching or electrical engagement with the adjacent face of the conductive pad 14 as shown in FIG. 11, depending upon the needs of the user.

An electrical lead 26 is electrically connected to each of the contact elements 24 by a respective one of the electrical wire conductors 28 and 30. To enhance the connection, each contact element 24 is provided with an extension 32 formed as a part thereof and having a wire receiving hole 34 therein in which the wire is received and to which the same may be soldered. The other ends of the wires 28 and 30 of the lead 26 may be electrically coupled to an appropriate monitor and/or instrumentation (not shown) to receive an indication of the flow of current or electrical resistance produced by the sensor 10. When the contacts 24 are molded with and as a unitary part of the dielectric member 16, their tab extensions 32 and connecting wires 28 or 30 will be permanently embedded in and molded as a part thereof.

The conductive sensor pad 14 is made relatively thin and may be even thinner than the member 16. In practice, it may be convenient to mold or cut out the same from a thin sheet of carbon impregnated silicone rubber so the same has two relatively spaced, substantially planar faces. The inner face 36 of the pad 14 is disposed facing the inner face 20 of the member 16 and may be positioned for electrical conducting engagement with the contacts 24 of the member 16. The outer face 38 of the sensor pad 14 will be positioned for attaching or affixing the sensor assembly 10 to a selected test site in the manner as will be described. In practice, the sensor pad 14 is made of a carbon impregnated silicone rubber material that functions as an excellent electrical conductor without restricting or inhibiting its flexibility.

Because of the poor bonding characteristics of silicone rubber, present known adhesives makes it difficult to apply adhesive tapes to the slippery surfaces of the silicone rubber that will enable it to be removably adhered directly to other surfaces, as the skin of the test site of a human. To overcome this problem, two discrete layers of double sided adhesive interface tapes 40 and 42 are applied to the outer face 38 in such manner as to define an exposed zone 44 on the face 38. The zone 44 provided by the double sided spaced tapes 40 and 42 defines an area at which electrical contact can and is made between the conductive pad 14 and the contact elements 24 during use and during operation of the sensor 10 as will be described.

Applied to the outer or exposed face of each tape 40 and 42 are complementary sized shaped and zone producing double sided tapes 46 and 48. Tapes 46 and 48, suitable for removable adhesion to the skin of the test site, may be comprised of such double sided tape known as Model No. 444 sold by Minnesota Mining and Manufacturing Company. Each such double sided tape 46 and 48 fits over and precisely covers respective tape layers 40 and 42 thereby maintaining the exposure of the zone 44.

The other inner face 36 of the sensor pad 14 is also coated with a double sided adhesive interfaced tape 50 preferably of the same construction as the interfaces 40 and 42. An outer complementary sized double sided tape 52 of the same material as the tapes 46 and 48 is adhered to the interface 50. Since the conductive sensor pad 14 is supplied as a discrete adhesively coated member to be discarded after use for sanitary reasons, it may be packaged separately from the assembled permanent electrode structure 12 with the exposed surfaces of the tapes 46, 48 and 52 protected by a releasable sanitized backing (not shown) or the whole may be contained within a sanitary or sterilized envelope or enclosure.

Referring now to FIGS. 8 through 12 inclusive, when a selected test site 54 is chosen on a portion of the body as illustrated in FIG. 8, the skin thereat is cleaned and sterilized in the usual manner. Assuming that the sensor pad 14 is not already affixed at 36 to the permanent electrode 12, it is removed from its packaging. It is then ready to be adhered to the inner face of the permanent electrode 12 at its zone defining double sided adhesive tapes 46 and 48. When so adhered to the inner face 20 of the permanent electrode 12, the assembly of the whole sensor 10 is complete to enable the same to be applied as a unit to the selected test site 54 on the skin.

Figure 10:
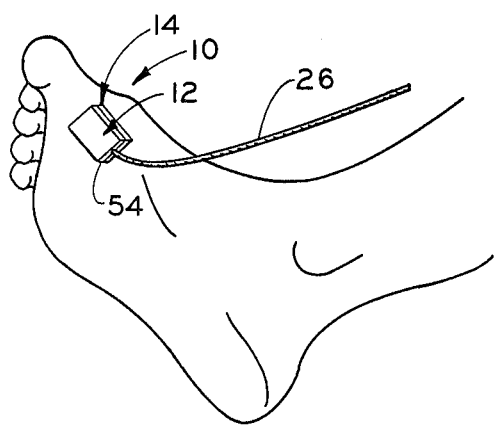

This is done by pressing the exposed adhesive surface of the tape 52 against the skin to cause the sensor 10 to adhere to the test site 54 as is shown in FIG. 10. When the zone defining tapes 46 and 48 are pressed into engagement with the inner face 20, the zone 44 is aligned with and positioned for engagement with the contact elements 24 of the electrode 12. This positions the smallest curved area 56 of the domes of the contacts 24 in or proximate to the zone 44 of the sensor pad 14 for touching engagement therewith.

Figure 12:
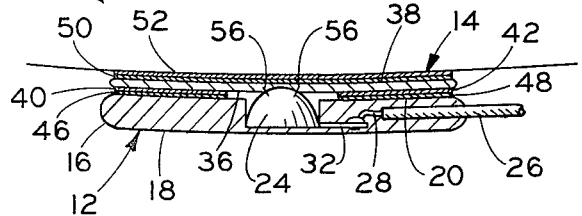
FIG. 12 is a view similar to FIG. 11 and illustrating the sensor when pressure is applied.

An electrical potential that is placed across the leads 28 and 30 will cause a current to flow when electrical engagement is made between the contacts 24 and the pad 14. When no pressure is applied across the sensor 10, and the contacts 24 are out of engagement with the zone 44 of the pad 14, no current will flow therebetween. As a force or pressure or compressive load is applied to the sensor 10, the contacts 24 and the pad 14 are moved into electrical engagement with each other. The sensor pad 14 experiences a lateral distention and enlarging envelopment of the contacts 24 as shown by the area of contact 56 as the curve of the dome of each of the contacts 24 and the associated engaging zone 44 of the sensor pad 14 are driven more firmly into engagement with each other as shown in FIG. 12. This effects a concomitant varying increase in the surface area of contact between the contacts 24 and the sensor pad 14 as seen by the increased area or extent of the contact lens 56 from that of FIG. 11 to FIG. 12.

As the area or extent of electrical contact increases, there is a resultant lowering of electrical resistance to the flow of current between the contacts 24 and the pad 14. This provides for and enables an increase in the flow of current through the contacts 24 of the sensor 10. Hence, the compression, force or pressure applied to the sensor 10 modulates and effects a change in its electrical resistance. Leads 28 and 30 apply and transmit this change in resistance or change in current flow to the appropriate monitoring apparatuses or instrumentation (not shown) with which they are connected.

When testing is finished and the need for the sensor 10 is completed, the sensor 10 may be removed from the test site 54 in any desired manner. This may be done by peeling the sensor 10 as a whole from the skin and then disposing of the pad 14 by peeling it from the electrode 12. Alternatively, the electrode 12 may be unpeeled from the sensor pad 14 at the adhesive tapes 46 and 48 while the pad 14 remains in its engagement with the skin of the body at the test 54 as in FIG. 9. The disposable sensor pad 14 then may be separated from the site 54 at the adhesive tape 52. This enables the reuse of the uncontaminated permanent electrode 12 because it is always free of touching contamination contact with the skin. Its reuse is enhanced by the application of a new sanitary sensor pad 14 to the same in the manner as previously described. This results in providing a permanently reusable sanitary electrode 12 that is available for affixation to and with inexpensive disposable electrode sensor pads 14.

In practice, it has been found that the change in the electrical resistance experienced by the sensor 10 is not an inverse linear function of the applied pressure, but is substantially logarithmic. Typically, this electrical resistance change varies from 1000 ohms and 100 ohms as the sensor 10 is actuated from a no-load condition to a maximum load condition. Indeed, the no-load or unloaded resistance can be an open circuit condition by simply assuring that the height or contact of the curved domes 24 are positioned away from initial electrical conductive engagement with the conductive sensor pad 14. By predeterminately controlling the geometry of the contacts 24 and their engagement with the sensor pad 14, the change of resistance with applied pressure can be made to assume other functions.

It is within the contemplation of the present invention that the geometric arrangement of the contacts 24 may be varied from that disclosed in the embodiment illustrated in FIGS. 1 to 12 inclusive. Further, the arrnagement of the electrical connections and their leads may be revised in accordance with the teaching of the invention. This is illustrated more fully in the embodiment shown in FIG. 13.

Figure 13:
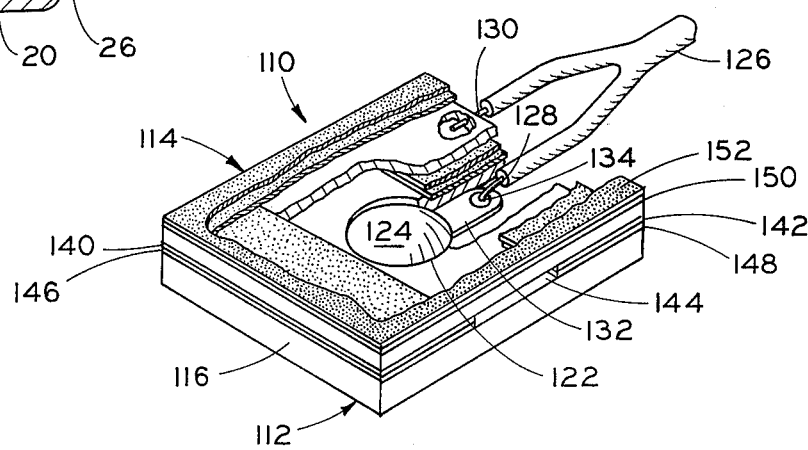
FIG. 13 is an enlarged perspective view of another embodiment of an assembled force sensor constructed according to the present invention with parts broken away.

The embodiment shown in FIG. 13 illustrates a force sensor assembly generally identified by the numeral 110. For ease of understanding and simplicity of description, correlation between the present embodiment 110 and that of the previously described embodiment 10, the structural elements contained in the present embodiment will be identified by numerals in the 100 series. The 10's digits thereof will correspond as closely as possible to the 10's digits used to identify like elements in the embodiment 10.

As in the prior embodiment 10, the permanent electrode of the present sensor 110 is generally identified by the numeral 112 while the sanitary disposable electrode is generally identified by the numeral 114. Because like parts of the present embodiment are related by 10's digits to those of the prior embodiment 10, it is possible to omit a description of such parts since the same will conform substantially to that already described with respect to the description of the embodiment 10. The permanent electrode 112 includes a non-conductive member 116 that is shown provided with a single electrical contact 124 positioned thereon rather than the double electrical contacts described with respect to the embodiment 10.

The single electrical contact is identified by the numeral 124 and, as in the prior described embodiment, it has a curved geometry or configuration facing in the direction of the engageable deformable surface 144 of the electrically conductive sensor pad 114. This assures that as a compression, force or pressure is applied to the sensor 110, the conductive sensor pad 114 will come into greater distorting and enveloping surface and area engagement with the curved surface of the electrical contact 124 of the permanent electrode 112 thereby to reduce the electrical resistance to the flow of current between the pad 114 and the contact 124. The structural details of the embodiment 110, being very much like those of the embodiment 10, will not be described other than to indicate that in the present embodiment the two wire electrical lead 126 has its conductors 128 and 130 connecedc across the contact 124 and the electrically conductive sensor pad 114. Thus, the lead 128 is connected with the contact 124 while the lead 130 is electrically conductively connected with the sensor pad 114.

Because the present force sensor 110 functions in essentially the same manner as the prior embodiment 10, a description of the same would be redundant. The differences between the two sensors reside in the use in the first described sensor 10 of the plurality of the electrically conductive contact elements 24 supported on and forming an integral part of the permanent electrode 112. Current transmitted through the contacts was then conveyed or supplied to an associated connected apparatus or instrumentation by way of the electrical lead 26 connected with each of the contact elements.

The present sensor embodiment 110 differs therefrom in that only one of the conductors 128 of the electrical lead 126 is connected with the electrical contact 124 forming a part of the permanent electrode 112. The second lead 130 of the electrical lead 126 is connected directly with the sensor pad 114. Thus, when the sensor pad 114 and the electrical contact 124 engage with each other and an electrical potential is applied across such leads, current will flow in proportion to the extent of contact or area between the two elements that are engaged with each other. The greater the area of contact the lower is the resistance to the flow of current across the leads of the wire 128.

Although in practice the sensor pad 114 may be disposable in the same manner as described with respect to the prior embodiment 10, it is more reasonable to assume that the present embodiment 110 may be reused as a completed assembly. In the event the same is reused as a completed assembly, the same may be subjected to sterilization procedures to assure that the application of the sensor pad 114 to the skin at the outer adhesive surface 152 will effect a sterile adhesion therebetween.

In the event the sensor pad 114 of the embodiment 110 is intended to be disposable, the same will be connected with the permanent electrode 114 in the same manner as previously described by the use of double sided pressure sensitive adhesive tapes 140, 142, 146, 148, 150 and 152. In the event the force sensor assembly 110 is to be used as a permanent structure wherein the sensor pad 114 forms an integral working part of the permanent electrode 112, it is then possible to bond the same together and to eliminate the need for the connecting double sided adhesive tapes 140, 142, 146 and 148.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A sensor comprising a member of dielectric material defined by inner and outer faces,
   electrical contact means on said member with a portion of said contact means substantially aligned with said inner face of said dielectric member, said electrical contact means being substantially noncompressible and of fixed conductivity, and
   a flexible conductive member defined by inner and outer faces, the inner one of which is attached to the face of said dielectric member to cover said electrical contact means such that, when a compressive load is applied to the sensor, the load induces an increase in the surface area of contact between facing portions of said conductive member and said contact means to effect a change in the electrical resistance thereacross in proportion to the extent of the applied load and independent of the location over the electrical contact means at which the load is applied.

2. The sensor of claim 1,
   electrical lead means electrically coupled to each of said contact means and conductive member to transmit current therefrom.

3. The sensor of claim 1,
   said contact means being of curved configuration and being positioned on said dielectric member such that the curved portion thereof is oriented toward and for movement into and out of increased engagement with said conductive member in response to an increase or decrease of the compressive load applied to said sensor.

4. The sensor of claim 3,
   wherein there are a plurality of said contact means each being of hemispherical shape,
   and electrical leads coupled electrically to each of said plurality of contact means to transmit current therefrom,
   said conductive member being movable into and out of increasing or decreasing electrical circuit completing engagement with and across said contact means according to a load applied to said sensor.

5. The sensor of claim 4,
   said dielectric and conductive members being of a flexible material.

6. The sensor of claim 5,
   releasable adhesive means between said dielectric and conductive members to releasably attach said conductive member to said dielectric member.

7. A force sensor comprising a disposable flexible relatively thin planar electrically conductive member, a relatively thin flexible permanent member of dielectric material having one face of which is substantially planar and adapted to be detachably affixed to one planar face of said conductive member, means on said permanent member positioning said electrical contact means and facing one planar face of said disposable conductive member such that the extent of electrical contact between said contact means and conductive member varies in accordance with the extent of a compressive load applied to said sensor to produce a corresponding electrical resistance therebetween, and means joining said disposable and permanent members together and being releasable to permit their separation and the disposal of said disposable member.

8. The sensor of claim 7, electrical load means electrically coupled to said electrical contact means and said conductive member to transmit current therefrom.

9. The sensor of claim 7, said electrical contact means being at least a pair of contact means each being of hemispherical configuration and each being positioned such that the curved portion of each said electrical contact means is directed toward and for varying areas of electrical circuit engagement with said one planar face of said conductive member to transmit varying amounts of current corresponding to that of the applied load.

10. A force comprising a thin flexible permanent electrode having a plurality of spaced electrical contacts supported thereon, a thin flexible conductive sensor pad defined by two faces, adhesive means applied to one face of said sensor pad and by which the same is electrically joined to a test site, adhesive means applied to the other face of said sensor pad to releasably affix the same to said permanent electrode and to define a non-adhesive zone thereon, said permanent electrode being oriented with respect to said other face of said sensor pad so as to place the electrical contacts in facing opposition to said zone such that when a compressive load is applied across the sensor, the load induces a change in the surface area of contact between facing portions of said zone of said sensor pad and said electrical contacts to correspondingly vary the electrical resistance thereacross.

11. The sensor of claim 10, said sensor pad being comprised of a conductive silicone rubber, said adhesive means being on each face of said sensor pad and comprising two stacked adhesive layers each adhered to the other to enable said sensor pad to be adhered to the test site and the other face of said sensor pad to be adhered releasably to said permanent electrode.

12. A pressure transducer comprising a dielectric electrode platform, electrical contact means on said platform, said contact means being substantially non-compressible and of fixed conductivity, a flexible conductive member facing said contact means so that the same move into varying extents of engagement in accordance with a pressure applied to the same to effect an electrical resistance that is a function of the pressure applied to the same and independent of the location over the contact means at which the pressure is applied, and electrical leads connected with said transducer to permit the transmission of said electrical resistance.

13. The transducer of claim 12, said electrical contact means being curved to present varying areas for engagement with said conductive member according to the applied pressure.

14. The transducer as in claim 13, said electrical contact means being of hemispherical shape.

15. The transducer of claim 13, said flexible conductive member being comprised of a carbon impregnated silicone rubber.

16. The transducer of claim 12, means releasably connecting together said conductive member and dielectric electrode platform to enable their separation and the disposal of said conductive member.

17. A sensor comprising a member of dielectric material defined by inner and outer faces, electrical contact means on said member with a portion of said contact means substantially aligned with said inner face of said dielectric member, a flexible conductive member defined by inner and outer faces, the inner one of which is attached to the face of said dielectric member to cover said electrical contact means such that, when a compressive load is applied to the sensor, the load induces an increase in the surface area of contact between facing portions of said conductive member and said contact means to effect a change in the electrical resistance thereacross in proportion to the extent of the applied load, and releasable adhesive means between said dielectric and conductive members to releasably attach said conductive member to said dielectric member.

18. The sensor of claim 17, said contact means being of curved configuration and being positioned on said dielectric member such that the curved portion thereof is oriented toward and for movement into and out of increased engagement with said conductive member in response to an increase or decrease of the compressive load applied to said sensor.

19. The sensor of claim 18, wherein there are a plurality of said contact means, each being of hemispherical shape, and electrical leads coupled electrically to each of said plurality of contact means to transmit current therefrom, said conductive member being movable into and out of increasing or decreasing electrical circuit completing engagement with and across said contact means according to a load applied to said sensor.

20. The sensor of claim 19, said dielectric and conductive members being of a flexible material.

21. A pressure transducer comprising a dielectric electrode platform, electrical contact means on said platform, a flexible conductive member facing said contact means so that the same move into varying extents of engagement in accordance with a pressure applied to the same to effect an electrical resistance that is a function of the pressure applied to the same, electrical leads connected with said transducer to permit the transmission of said electrical resistance, and means releasably connecting together said conductive member and dielectric electrode platform to enable their separation and the disposal of said conductive member.

22. The transducer of claim 21, said electrical contact means being curved to present varying areas for engagement with said conductive member according to the applied pressure.

23. The transducer as in claim 22, said electrical contact means being of hemispherical shape.

24. The transducer of claim 22, said flexible conductive member being comprised of a carbon impregnated silicone rubber.

* * * * *